(12) United States Patent
Truog

(10) Patent No.: US 7,611,729 B2
(45) Date of Patent: Nov. 3, 2009

(54) DOSAGE FORMS HAVING PROLONGED ACTIVE INGREDIENT RELEASE

(75) Inventor: Peter Truog, Basel (CH)

(73) Assignee: Lunamed AG (CH)

( * ) Notice: Subject to any disclaimer, the term of this patent is extended or adjusted under 35 U.S.C. 154(b) by 286 days.

(21) Appl. No.: 10/488,276

(22) PCT Filed: Sep. 4, 2002

(86) PCT No.: PCT/CH02/00486

§ 371 (c)(1),
(2), (4) Date: Feb. 26, 2004

(87) PCT Pub. No.: WO03/022253

PCT Pub. Date: Mar. 20, 2003

(65) Prior Publication Data

US 2004/0180962 A1 Sep. 16, 2004

(30) Foreign Application Priority Data

Sep. 10, 2001 (EP) .................................. 01810865

(51) Int. Cl.
*A61K 9/22* (2006.01)
*A01N 61/00* (2006.01)
*A61K 31/00* (2006.01)

(52) U.S. Cl. .......................................... 424/468; 514/1

(58) Field of Classification Search .................. 424/468
See application file for complete search history.

(56) References Cited

U.S. PATENT DOCUMENTS

| | | | |
|---|---|---|---|
| 4,457,942 A | 7/1984 | Brusilow | |
| 5,569,680 A | 10/1996 | Wu | |
| 5,654,333 A | 8/1997 | Samid | |
| 5,661,179 A | 8/1997 | Samid | |
| 5,710,178 A | 1/1998 | Samid | |
| 5,912,269 A | 6/1999 | Tung et al. | |
| 5,945,407 A | 8/1999 | Bemis et al. | |
| 5,972,995 A | 10/1999 | Fischer et al. | |
| 6,011,000 A | 1/2000 | Perrine et al. | |
| 6,037,376 A | 3/2000 | Samid | |
| 6,207,195 B1 | 3/2001 | Walsh et al. | |
| 6,362,226 B2 | 3/2002 | Phillips, III et al. | |
| 6,372,938 B1 | 4/2002 | Burzynski et al. | |
| 6,403,646 B1 | 6/2002 | Perlmutter et al. | |
| 6,495,719 B2 | 12/2002 | Lan-Hargest et al. | |
| 6,635,632 B1 | 10/2003 | Wu et al. | |
| 6,656,912 B2 | 12/2003 | Perlmutter et al. | |
| 2002/0115619 A1* | 8/2002 | Rubenstein et al. | 514/27 |
| 2002/0143037 A1 | 10/2002 | Lan-Hargest et al. | |
| 2002/0143052 A1 | 10/2002 | Lan-Hargest et al. | |
| 2002/0143196 A1 | 10/2002 | Lan-Hargest et al. | |
| 2003/0083521 A1 | 5/2003 | Lan-Hargest et al. | |
| 2003/0096762 A1 | 5/2003 | Fischer et al. | |
| 2003/0114525 A1 | 6/2003 | Kammer et al. | |
| 2003/0125306 A1 | 7/2003 | Lan-Hargest et al. | |
| 2003/0166554 A1 | 9/2003 | Cohen et al. | |
| 2003/0195256 A1 | 10/2003 | Singh | |
| 2004/0044049 A1 | 3/2004 | Pei et al. | |
| 2004/0077591 A1 | 4/2004 | Dangond | |
| 2004/0142859 A1 | 7/2004 | Steffan et al. | |

FOREIGN PATENT DOCUMENTS

| | | |
|---|---|---|
| EP | 1 249 246 A1 | 4/2001 |
| EP | 1 206 936 A2 | 5/2002 |
| EP | 1 232 746 A1 | 8/2002 |
| WO | WO 85/04805 A1 | 11/1985 |
| WO | WO 93/07866 A2 | 4/1993 |
| WO | WO 95/10271 A3 | 4/1995 |
| WO | WO 95/10281 A1 | 4/1995 |
| WO | WO 96/27369 A2 | 9/1996 |
| WO | WO 98/40078 A1 | 9/1998 |
| WO | WO 98/56370 A2 | 12/1998 |
| WO | WO 99/37150 A1 | 7/1999 |
| WO | WO 00/18394 A1 | 4/2000 |
| WO | WO 00/56153 A1 | 9/2000 |
| WO | WO 01/52830 A2 | 7/2001 |
| WO | WO 01/97791 A2 | 12/2001 |
| WO | WO 00/18394 A1 | 4/2002 |
| WO | WO 02/056823 A2 | 7/2002 |

(Continued)

OTHER PUBLICATIONS

Remington's Pharmaceutical Sciences (18th Ed, MACK publishing Co., 1990) Chpt 89 and 90.*

(Continued)

*Primary Examiner*—Michael G Hartley
*Assistant Examiner*—Melissa Perreira
(74) *Attorney, Agent, or Firm*—Porzio, Bromberg & Newman P.C.

(57) ABSTRACT

The present invention relates to prolonged-release oral dosage forms of 4-phenylbutyric acid salts, such as sodium 4-phenylbutyrate. The prolonged release oral dosage forms are preferably tablets. The prolonged release is achieved by formulating 4-phenylbutyric acid with a delaying matrix material, such as hydroxypropylmethyl cellulose. The prolonged release oral dosage forms of the present invention may be administered once or twice a day to a patient suffering from a disease such as cancer or a urea cycle disorder.

6 Claims, No Drawings

FOREIGN PATENT DOCUMENTS

| WO | WO 02/066672 A2 | 8/2002 |
| --- | --- | --- |
| WO | WO 02/076941 A2 | 10/2002 |
| WO | WO 02/083173 A1 | 10/2002 |
| WO | WO 02/090534 A1 | 11/2002 |
| WO | WO 03/022253 A1 | 3/2003 |
| WO | WO 03/066035 A2 | 8/2003 |

OTHER PUBLICATIONS

UcyclydPharma www.buphenyl.com/about_buphenyl.htm Jun. 21, 2006.*

Brettman, L.R., et al., "Pharmacokinetics and safety of single oral doses of VX-366 (isobutyramide) in healthy volunteers," *J. Clin. Pharmacol.*, 36(7):617-622 (Jul. 1996).

Brusilow, S.W., et al, "Urea cycle disorders: Diagnosis, pathophysiology, and therapy," *Adv. Pediatr.*, 43:127-170 (1996).

Chang, S.M., et al, "Phase II study of phenylacetate in patients with recurrent malignant glioma: A North American Brain Tumor Consortium Report," *J. Clin. Oncol.*, 17(3):984-990 (Mar. 1999).

Collins, A.F., et al., "Oral sodium phenylbutyrate therapy in homozygous beta thalassemia: a clinical trial," *Blood*, 85(1):43-49 (Jan. 1, 1995).

Desmet, G., et al., "Pharmacokinetics of butyric acid derivative with xylitol," *Eur. J. Drug Metabol. Phar-macokinet*, 3:348-351 (1991).

Fibach, E., et al, "Enhanced fetal hemoglobin production by phenylacetate and 4-phenylbutyrate in erythroid precursors derived from normal donors and patients with sickle cell anemia and beta-thalassemia," *Blood*. 82(7):2203-2209 (Oct. 1, 1993).

Gilbert, J., et al., A phase I dose escalation and bioavailability study of oral sodium phenylbutyrate in patients with refractory solid tumor malignancies, *Clin. Cancer Res.*, 7(8):2292-2300 (Aug. 2001).

Gore, S.D., et al., Impact of the putative differentiating agent sodium phenylbutyrate on myelodysplastic syndromes and acute myeloid leukemia, *Clin. Cancer Res.*, 7(8):2330-2339 (Aug. 2001).

Johnstone, R.W., "Histone-deacetylase inhibitors: Novel drugs for the treatment of cancer," *Nat. Rev. Drug Discovery*, 1(4):287-299 (Apr. 2002).

Lu, Q., et al., "Zn2+-chelating motif-tethered short-chain fatty acids as a novel class of histone deacetylase inhibitors," *J. Med. Chem.*, 47(2):467-474 (Jan. 15, 2004).

MacMillan, M.L., et al., "Treatment of Two Infants with Cooley's Anemia with Sodium Phenylbutyrate," *Ann. N. Y. Acad. Sci.*, 850:452-454 (Jun. 30, 1998).

Pellizzaro, C., "Cholesteryl butyrate in solid lipid nanospheres as an alternative approach for butyric acid delivery," *Anticancer Res.*, 19(5B):3921-3925 (Sep.-Oct. 1999).

Perlmutter, D.H., "Chemical Chaperones: A Pharmacological Strategy for Disorders of Protein Folding and Trafficking," *Pediatric Research*, 52(6):832-836 (Dec. 2002).

Planchon, P., et al., "Differential elimination of synthetic butyric triglycerides in vivo: a pharmacokinetic study," *J. Pharm. Sci.*, 82(10):1046-1048 (Oct. 1993).

Pouillart, P., et al. "Butyric monosaccharide ester-induced cell differentiation and anti-tumor activity in mice. Importance of their prolonged biological effect for clinical applications in cancer therapy," *Int. J. Cancer*, 49(1):89-95 (Aug. 19, 1991).

Pouillart, P., et al, "Pharmacokinetic studies of N-butyric acid mono- and polyesters derived from monosaccharides," *J. Pharm. Sci.*, 81(3):241-244 (1992).

Resar, L.M., et al., "Induction of fetal hemoglobin synthesis in children with sickle cell anemia on low-dose oral sodium phenylbutyrate therapy," *J. Pediatr. Hematol. Oncol.*, 24(9):737-741 (Dec. 2002).

Rubenstein, R.C., et al., "Sodium 4-phenylbutyrate downregulates Hsc70 Implications for intracellular trafficking of ΔF508-CFTR," *Am. Physiol. Soc.*, 278(2):C259-C267 (Feb. 2000).

Sung, M.W., and Waxman, S., "Chemodifferentation Therapy with Fluorouracil (FU) and Phenyl-butyrate (PB) in Advanced Colorectal Cancer: a Phase I Trial," *Proc. Am. Assoc. Cancer Res.*, 40:339 Abstract No. 2245 (Mar. 1999).

Virgushin, D.M., et al, "Targeted histone deacetylase inhibition for cancer therapy," *Curr. Cancer Drug Targets*, 4(2):205-218 (Mar. 2004).

\* cited by examiner

DOSAGE FORMS HAVING PROLONGED ACTIVE INGREDIENT RELEASE

RELATED APPLICATIONS

This is a National Stage of International Application Number PCT/CH02/00486, filed Sep. 4, 2002, which claims priority of EP patent application 01810865.4 filed Sep. 10, 2001.

FIELD OF THE INVENTION

The invention relates to solid, orally administrable pharmaceutical dosage forms having prolonged active ingredient release for once or twice daily administration, containing a 4-phenylbutyric acid salt as active ingredient, to methods for producing them and their use for treating various diseases, known to be beneficially influenced by the active ingredient.

BACKGROUND OF THE INVENTION

The 4-phenylbutyric acid sodium salt (sodium 4-phenylbutyrate) and its use for the treatment of a variety of illnesses, such as benign prostate hyperplasy, cancer, cystic fibrosis; HIV, kidney and liver failures, thalassemia and urea cycle disorders are known. For example, WO 85/04805 (Brusilow) discloses a process for waste nitrogen removal In human beings, wherein 4-phenylbutyrate is administered. DE 19,810,383 (Manhart, et. al.) describes 4-phenylbutyrate as apoptosis inducing agent for neoplastic therapy. WO 9937150 (Pandolfi et al.) describes a transcription therapy for cancers using a retinoic acid and/or an inhibitor of histone deacetylase. WO 93/07866, WO 9510271 or EP 725635 (Samid) disclose compositions and methods using phenylacetic acid derivatives for therapy and prevention of a number of pathologies, Including cancer, AIDS, anemia, and severe beta-chain hemoglobinopathies, which emerged in a number of U.S. patents. WO 9856370 (U.S. Pat. No. 6,207,195, Walsh et.) describes therapeutic sodium 4-phenylbutyrate containing nanospheres for treatment of cystic fibrosis by CFTR gene therapy. WO 9840078 (Rephaeli) discloses therapeutic augmentation of oxyalkylene diesters and butyric acid derivatives with inhibitors of fatty acid beta-oxidation.

4-Phenylbutyric acid is rather quickly broken down in the human body by beta-oxidation to phenylacetic acid. This acid eliminates glutamine from cells, which is essential for the growth of cancer. A deficiency of glutamine in cancer cells results in apoptosis. In order to counteract the fast elimination of 4-phenylbutyrate from the body, about 10 to 40 g per patient and day are administered. In order to attain and maintain constant levels of the active ingredient in the plasma also infusion solutions are used. These, however, are unsuitable for ambulant treatment. The use of large amounts of 4-phenylbutyrate is also a commercial problem. The active compound is very expensive and has to be taken for several months up to years.

Accordingly, it would be desirable to have a 4-phenylbutyrate formulation that avoids the problems associated with application of large amounts of this compound. The formulation should be effective with lower amounts of the active ingredient. On repeated administration constant therapeutically effective plasma levels should be provided; exhibiting a minimum of fluctuations between the maximum and minimum concentrations of active Ingredient in the blood. A possible method of reducing the influx time of the active ingredient and of minimising fluctuations may be achieved by controlling the dissolution of the active ingredient over a longer period of time than is the case with conventional formulations. A solution to this problem is offered by the therapeutic system OROS® (F. Theeuwes, J. Pharm. Sci., Vol. 64, 12, 1987-1991, 1975). A disadvantage of the OROS systems is that they are technically difficult to produce.

A formulation would be desirable with a slow release rate providing low plasma level fluctuations, which remain constant over a relatively long period. Slow release formulations or retard formulations are known in the pharmaceutical art. However, they cannot simply be used for particular problems, but have to be individually designed for each active ingredient and for each indication. This requires some inventive ingenuity.

The release rate of the active ingredient from tablets or powders is influenced by the solubility characteristics of the active ingredient, which, in turn, depend upon solubility, particle size, specific surface area and interactions with other excipients. Dissolution may be retarded by means of diffusion barriers in the core of the tablet or in a film coating. Retarding dissolution by means of diffusion barriers in the core is a principle that is frequently used on account of its technical simplicity. It is possible to use various excipients, for example swelling agents, lipophilic substances or alternatively plastics, as diffusion barriers. The matrix, that is to say the homogeneous substance composition, can be such that the release of the active ingredient takes place by diffusion of the dissolved active ingredient, especially through the water-filled pores in the tablet core and if required in special cases by diffusion through the retarding substance which must for that purpose be in a suitable structural form. Alternatively the matrix also can be in a form that is subjected to slow erosion and in this way effects delayed release of the active ingredient.

In all those cases the diffusion path and the active diffusion surface for the release change with time. For that reason it is clear that with matrix systems neither in vivo nor in vitro is it usually possible to expect any release having linear kinetics, that is to say of the $0^{th}$ order. Instead, the release is generally a function of the root of the time (Square root dissolution; Higuchi; J. Pharm. Sci. 52, 12, 1963, 1145). The validity of the Higuchi law for the hydrocolloid matrix has also been documented in numerous publications (Ford et al., Int. J. Pharm., 24, 1985, 327-338; 339-350; 1985).

Therapeutic dosage forms in which the medicinal substance is incorporated into a soluble or erodible matrix would be desirable on account of the ease of their manufacture, the low degree of variation between different manufacturing processes and because of the relatively low costs.

The use of hydrophilic gums, such as hydroxypropylmethyl-cellulose, as delaying matrix material is known and has been tested with a large number of active ingredients. No formulation has been disclosed hitherto that would be suitable for attaining the desired objectives with 4-phenylbutyrates.

The behaviour of a specific medicinal substance when combined with a retarding excipient cannot be calculated or generally predicted. Although the basic factors affecting release from matrix systems have been well researched, interactions between the retarding material on the one hand and the active ingredient and other excipients on the other can affect the retarding action in various ways.

The question of release kinetics is a multi-factored problem. Responsible factors are, in addition to the dissolution properties of the active ingredient, the rate of water absorption and thus the rate of swelling of the Interface to be penetrated, the diffusion co-efficient of the substance through the swollen mass and also the time-dependent thickness thereof. It can clearly be imagined that release of the $0^{th}$ order is brought about by the existence of an equilibrium between the erosion of the tablet and the dissolution properties of the active ingredient, so that the diffusion paths for the substance remain constant during the dissolution time.

However, it is important to realise that it is impossible to predict, whether the release rate will be of the $0^{th}$ or any other order. From the large number of known pharmaceutical excipients it is necessary to select those suitable for the desired purpose and to, process them in suitable quantity ratios, which must likewise be selected, to form an effective matrix system.

PROBLEM OF THE INVENTION

The problem underlying: the present invention was to overcome the existing drawbacks of using 4-phenylbutyrate salts in alleviating and curing a variety of diseases. As the substance and its beneficial healing capacity was known for a long time there must have been prejudices for developing a solid, orally administrable pharmaceutical dosage form that is technically easy and cheaply to produce and which exerts its therapeutic effects upon oral once or twice daily application in lower than usual amounts.

A pharmaceutical dosage form, fulfills the requirements of reducing the dosage without reducing the therapeutic activity, which can be more easily and more cheaply produced, and which can be more easily applied also during prolonged ambulant treatment, is quite often a lucky strike. The treatment of patients, and the surprising success achieved therewith can be used as a measure for inventive step.

Such surprising dosage form is provided by the present invention.

DETAILED DESCRIPTION OF THE INVENTION

The invention relates to a pharmaceutical unit dosage form comprising a therapeutically effective amount of a. 4-phenylbutyric acid salt, having prolonged release of the active ingredient, and being suitable for alleviating and curing various diseases of a human patient upon once or twice daily oral administration to said patient.

Pharmaceutical unit dosage forms are especially tablets and powders introduced into capsules, for example hard gelatine capsules.

Salts of 4-phenylbutyric acid may be of the alkaline or earth alkaline type, e.g. lithium, sodium, potassium, magnesium or calcium. Preferred is the sodium salt. The unit dosage form contains-about 50 to 1000-mg, preferably about 100 to 500 mg, most preferably about 250 mg of the active compound.

By prolonged release of the active ingredient is to be understood especially a rate of release of the active ingredient during a period of about 6 to 12 or up to 24 hours.

The prolonged release dosage form or retard form is a homogeneous matrix in powder or preferably in tablet form comprising about 20-80%, preferably about 35% by weight of a 4-phenylbutyric acid salt.

The term "about" as used hereinbefore and hereinafter in connection with weights or other measures should indicate a possible aberration of between +/−5 to 10%.

The matrix is provided by about 5-50%, preferably about 20% by weight of hydroxypropylmethylcellulose having a molecular weight in the range of about 20,000-250,000, and, in dependence upon the nature of the retardation of release desired, 2-25% by weight of excipients controlling release and optionally other pharmaceutically acceptable excipients making up the weight of the dosage form to 100%.

A therapeutically effective amount is the amount required for maintaining the desired therapeutic effect, in particular of inhibiting glutamate metabolism, over a period of about 24 hours. The therapeutically effective amount of the hitherto known dosage forms is 10,000 to 40,000 mg per, day. In the present invention the effective daily amount is significantly reduced. One dosage unit form contains from about 20 to 1000 mg of the 4-phenylbutyrate, preferably about 250 mg. The effective dose upon twice daily administration amounts to merely 40 to 2,000 mg, preferably 500 mg per day.

A matrix is defined in galenical pharmacy as being a well mixed, homogeneous substance composition that can be compressed to form tablets or can be introduced in the form of a powder into capsules, preferably hard gelatine capsules.

The tablets or capsules contain, for example, 100-500 mg, preferably 250 mg, of active ingredient, for example sodium 4-phenylbutyrate.

The release controlling pharmaceutically acceptable excipients are lipophilic or hydrophilic substances (release retarders, liberation controllers) that modify the swelling process of the retarding matrix.

Hydrophilic release retarders are solid polyethylene glycols, for example polyethylene glycol 4,000 or 6,000, or polyvinyl-pyrrolidones, for example Kollidone 25®, Kollidone 30® or Kotlidone 90® (brand names of BASF GmbH) with various viscosities, and also vinylpyrrolidone/vinyl acetate copolymers, for example Kollidone VA 64® (brand name BASF GmbH).

Lipophilic release retarders are pharmaceutically acceptable derivatives of vegetable fats in solid tablet form with a melting point of above 60°, such as vegetable fatty acids with chain lengths of at least 16 carbon atoms, for example stearic acid C16, palmitic acid C18 or mixtures thereof, and especially vegetable oils hardened by hydrogenation, for example hydrogenated castor oil, such as Cutina HR® (brand name of Henkel) or hydrogenated cottonseed oil, such as Emvelop® or Lubritab® (brandnames of Mendell). For the preparation of tablets the lipophilic release retarders must be suitable for tabletting. About 2-25% release retarder are used, based on the final weight of the tablet or capsule.

The hydroxypropylmethylcellulose (HPMC) preferably used according to the invention and representing the retarding principle, is of the 2208 USP XXII type, has a molecular weight of 20,000-250,000, preferably 20,000-120,000, and has a preferred viscosity of 100-15,000 cps. Especially suitable are Methocel K® types which produce the fastest swelling, for example Methocel K100M Premiums (Prochem Chemical Co.), Methocel KIOLV®, Methocel K4M® and Methocel K15M® (brand names, DOW CHEMICAL CO.) or the virtually equivalent Metolose 90SH® types, for example Metolose 90SH100®, Metolose 90SH4,000® and Metolose 90SH15,000® (brand names, Shin-Etsu Chemical Co. Ltd.). Approximately 5-50% by weight, preferably 10-40% by weight, HPMC are used, based on the final weight of the tablet or capsule filling.

Further excipients are certain fillers, lubricants and flow-regulating agents, which may likewise exert an effect, albeit a small one, on the release kinetics.

Fillers are corn starch, lactose, microcrystalline cellulose, mannitol or dicalcium phosphate, and also mixtures thereof. Useful is for example a mixture of 75% lactose and 25% microcrystalline cellulose, for example Cellactose® (brand name of Meggle GmbH). The fillers must be carefully selected in suitable amounts and matched exactly to specific formulation. In addition, attention should be paid to the compression properties. They are used in an amount making up the weight of the tablet to 100%;

Lubricants are, for example, magnesium stearate, stearic acid of a suitable quality, calcium stearate, and mixtures thereof, magnesium stearate being preferred, and are preferably used in an amount of 0.1-1%, based on the final weight of the formulation.

Suitable agents that act on the flowability of the powder to be encapsulated or compressed (flow-regulating agents) are, for example, highly dispersed silicon dioxide, preferably in an amount of 0.25-1%, based on the final weight of the formulation.

The tablets can be provided with a neutral film coating or with a film coating that delays the release of the active ingredient, that is to say that produces a lag time. A stomach resistant film coating is preferred.

A film coating having no retarding action consists, for example, of film-formers, pigments, anti-adhesive agents and plasticisers. Such a film former may consist of fast-dissolving constituents. In this case it is preferable to use low-viscosity hydroxypropylmethylcellulose type 2910 USP XXII, for example Methocele® E5 or E 15 (Dow Chemicals Ltd.) or Pharmacoaet® 606 (Shin-Etsu).

A film coating having retarding action may consist of water-insoluble but water-permeable polymers which, as a diffusion barrier, not only bring about a lag time at the beginning but also affect the swelling behaviour of the core over a prolonged period as a result of the initially altered water permeation. Preferred water-insoluble polymers are water-insoluble derivatives of methacrylic acid, for example methyl/ethyl acrylate, such as Eudraget® RS or RL and Eudragit® NE (brand names, Rohm Pharma GmbH) and mixtures thereof.

The film coating may also contain excipients customary in film-coating procedures, such as light-protective pigments, for example iron oxide, in an amount of about 40-80%, or titanium dioxide, in an amount of about 100-150%, anti-adhesive agents, for example talc, in an amount of about 50-200%, and also suitable plasticisers, matched to the polymer, of the polyethylene glycol series, for example PEG 400 or PEG 6,000, or triethyl citrate in the case of films based on methacrylic acid derivatives, such as Eudragit® RSIRL and NE, in an amount of about 30-60% (percentages are in each case based on the dry coating substance). When aqueous dispersions of the said Eudragit® types are used, then, for example, Tween 80 is necessary as aggregation inhibitor.

For the preparation of the powder components for filling hard gelatine capsules it is possible to use the same powder components as those used for the preparation of tablets. The release kinetics in tablets are also dependent upon geometric factors, such as the shape and size of the tablets. Biconvex tablets having a diameter of approximately 5-11 mm, especially 7-9 mm, and a thickness of 3-10 mm, especially 6.8 mm, are preferred.

A preferred tablet contains, for example:
about 250 mg of sodium phenylbutyrate,
about 146 mg of hydroxypropylmethylcellulose type 2208 USP XXII of 100 or 4000 cps,
about 261 mg of lactose,
about 30 to 60 mg, in particular 31.25 mg, of microcrystalline cellulose (Avicel® PH 102, Select chemie, or Cellactose®, Meggle),
about 10 mg of hardened vegetable oil, or e.g. talcum,
about 1.5 mg of magnesium stearate, and
optionally about 1 mg of highly dispersed silicon dioxide, so that cores prepared thereof weigh about 0.7 g.

Advantageously, a number of 24,000 of the cores are provided with a film coating for example by using a colloidal dispersion containing about 7,850 g of isopropyl alcohol, about 3,360 of Eudragit®L 12.5, about 66 g of dibutyl phthalat, about 18.0 g of Miglyol® 812 and about 56 g of polyethyleneglycol PEG 400.

For tablets containing 100 and 500 mg of active ingredient, corresponding aliquots of the excipients should be used.

Preferred pharmaceutical dosage forms contain 250 mg of sodium 4-phenylbutyrate, and are specifically the tablets described in Example 1.

In a further embodiment the invention relates also to a process for the preparation of a pharmaceutical dosage form according to the above description, characterised in that the dosage form is prepared in a conventional manner.

The constituents of the tablet cores are, if necessary, ground to the desired particle size, mixed homogeneously with one another at the same time or in a specific sequence and, optionally, granulated by moistening with water, dispersing and drying the granular mass. If the mixture is granulated, the fillers, flow agents and lubricants can be added to the granules after granulation. The mixture of the core constituents is compressed to form tablets having a hardness of approximately 50-100 N, preferably 90 N, or may be introduced as such into hard gelatine capsules.

The film-coating is effected in a conventional manner by mixing the constituents of the film coating with water, coating the compressed tablet cores therewith and drying at approximately from 30 to 40° C., preferably approximately 35° C.

In a further embodiment the invention relates to the use of a pharmaceutical dosage form in accordance with the present invention for the treatment of diseases that can be influenced by said dosage form, comprising the once or twice daily oral administration of a pharmaceutical dosage form according to the present invention to a patient in need thereof and to be treated.

Depending upon the age and weight of the patient, the nature and severity of the illness, as well as the general condition of the patient, and also on the salt of the 4-phenylbutyric acid to be administered, the dosage forms used contain about 100 to about 1,000 mg, preferably 250 mg of active ingredient.

Diseases that can be beneficially influenced by the present dosage form include in particular benign prostate hyperplasy, cancer, leukemias, cystic fibrosis, AIDS, kidney and liver diseases, thalassemia and urea cycle disorders. For example, the treatment of an adenocarcinoma of the prostate can be carried out by administering twice daily, e.g. in the morning and evening, a pharmaceutical tablet formulation containing 250 mg of sodium 4-phenylbutyrate. The therapeutic effect is evident after treatment of about one month when the pains disappear. Treatment may be continued for several month or years until a satisfactory effect is observed or the patient is total free of the disease. The 4-phenylbutyrate exerts no side effects even over a long period of treatment.

The following Examples illustrate the invention but do not constitute a limitation thereof.

EXAMPLE 1

Production of Slow Release Tablet with 250 mg of Sodium 4-Phenylbutyrate

A mixture of 6,000.0 g of sodium 4-phenylbutyrate from Triple Crown America, Inc., 6,280.0 g of lactosum monohydricum 3,500.0 g of Methocel K100 M Premium (Prochem), and 750.0 g of Avicel PH 102 (Select Chemie) is wettened with 4,000.0 g of aqua purificata (water purified by inversion osmosis) and dried in cold air during 18 hours. The mixture is forced through a sieve IV mm and dried again during 10 hours with air of 40° C. A mixture of 240.0 g of talcum and 30.0 g of magnesium stearate is admixed during 20 minutes and the mixture is pressed into tablets of 0.70 g each, a thickness of about 6.8 mm and with a hardness of 90 Newton. Yield: 24,000 tablet cores.

The mixing is carried out with a Diosna Mixer, the drying in a Lükon drying cabinet, the sieving with a Köhler & Bosshard sieving machine, and the tablet pressing with a Korsch tablet press EK II.

The cores are provided with a film coating for example by using a colloidal dispersion containing 7,850 g of isopropyl alcohol, 3,360 g of Eudragit L 12.5, 66 g of dibutyl phthalate, 18.0 g of Miglyol 812, and 56 g of polyethylene glycol PEG 400. The suspension is sprayed at 3.5 at 0 and 25° C. onto the 24,000 cores. The film-coated tablets are dried in a circulating air drying cabinet for at least 4 hours at 35° C.

EXAMPLE 2

Human Test Results

Following are descriptions of treatments and test results obtained from human patients.

Patent Nr. 1, MM, Born Feb. 5, 1909:

This patient presented on Apr. 24, 1995 with a cancer of the prostate with a prostate specific antigen (PSA) of 36 µg/l and with positive prostate biopsies, revealing adenocarcinoma of the prostate. The positive bone scan revealed multiple bone metastasis with lumbar and thoracic spine, ribs and pelvis. Because of progressive bone pains he underwent bilateral orchiectomy in February 1996. He became free of pain until November 1998 when he again suffered bone pains mainly in his back. He was than treated orally twice daily with 250 mg of sodium phenylbutyrate retard tablets according to Example 1. Four weeks later he was free of pain. He stayed on this medication until June 2001 without any other symptoms of the prostate carcinoma. The PSA and the alkaline phosphatase were always within normal limits. No side effects attributable to the treatment have been observed.

A work-up in June 2002 revealed no symptoms of signs of an active prostate carcinoma. He stays now in complete unmaintained remission for 12 months.

Patient Nr. 2, KR, Born Jul. 24, 1919:

This patient presented in March 1997 with a pathological fracture of the 8$^{th}$ thoracic vertebra caused by metastatic destruction. The multiple biopsies of the slightly enlarged prostate was positive for adenocarcinoma on both sides. The bone scan showed multiple uptake in ribs and vertebrates. On Apr. 10, 1997 he underwent bilateral orchidectomy. From May 1997 until September 2000 he was treated orally twice daily with 250 mg of sodium 4-phenylbutyrate retard tablets according to Example 1. The last control in August 2001 revealed no symptoms. The bone scan showed no pathological uptakes. The 4-phenylbutyrate was well tolerated without side-effects.

After 20 months in unmaintained remission he died from a secondary disease. His post mortem examination revealed histological no tumor tissue in the prostate or elsewhere.

Patient Nr. 3, M.W., Born Mar. 11, 1911:

In October 1997 a biopsy of the prostate due to elevated PSA (17.5 µg/l) revealed a cancer of the prostate. He was treated with a LH-RH agonist (Decapeptyl retard monthly). During 1998 his-alkaline phosphatase begun to raise from 132 up to 167 U/I (normal value <110 U/I). Beginning in November 1998, he was treated orally twice daily with 250 mg of sodium 4-phenylbutyrate according to the retard tablets of Example 1. His PSA dropped to unmesurable levels and his alkaline phosphatase dropped gradually to 114 U/I on Dec. 14, 1999. He never complained about bone pain. He died on Apr. 24, 2000, due to heart attack with congestive heart failure. The phenylbutyrate was well tolerated without side-effects.

The invention claimed is:

1. A prolonged release oral pharmaceutical dosage form of a 4-phenylbutyric acid salt comprising:
   250 mg of a 4-phenylbutyric acid salt;
   wherein the dosage form comprises 146 mg of hydroxypropylmethylcellulose, 261 mg of lactose, 30 to 60 mg of microcrystalline cellulose, 10 mg of hardened vegetable oil or talcum, 1.5 mg of magnesium stearate, and optionally about 1 mg of highly dispersed silicon dioxide, that permits a rate of release of 4-phenylbutyric acid during a period of about 6 to 24 hours.

2. The prolonged release oral pharmaceutical dosage form of claim 1, wherein the tablet weighs 0.7 g.

3. The prolonged release oral pharmaceutical dosage form of claim 1, wherein the tablet further comprises a film coating.

4. A method to treat a patient suffering from adenocarcinoma of the prostate comprising administering the prolonged release oral pharmaceutical dosage form of claim 1 twice a day.

5. The method of claim 4, wherein the effective dose upon twice daily administration to a patient is about 250 to about 2000 mg per day.

6. The prolonged release oral pharmaceutical dosage form of claim 1, wherein the 4-phenylbutyric acid salt is sodium 4-phenylbutryate.

* * * * *